United States Patent
Conzone et al.

(10) Patent No.: US 9,782,542 B2
(45) Date of Patent: *Oct. 10, 2017

(54) SELF-LUBRICATING PHARMACEUTICAL SYRINGE STOPPERS

(71) Applicant: Momentive Performance Materials Inc., Waterford, NY (US)

(72) Inventors: Samuel Conzone, Castleton, NY (US); David M. Rusinko, North Royalton, OH (US); Chandrashekar Raman, Sheffield Village, OH (US); Indumathi Ramakrishnan, Bangalore (IN); Anantharaman Dhanabalan, Bangalore (IN); Mayank Kumar Dubey, Bangalore (IN); Markus Bley, Dusseldorf (DE); Hans Rafael Winkelbach, Burscheid (DE)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/968,974

(22) Filed: Aug. 16, 2013

(65) Prior Publication Data
US 2013/0338606 A1  Dec. 19, 2013

Related U.S. Application Data

(63) Continuation-in-part of application No. 13/227,625, filed on Sep. 8, 2011, now Pat. No. 8,530,536, which
(Continued)

(51) Int. Cl.
*A61M 5/315* (2006.01)
*C10M 169/04* (2006.01)
*A61M 5/31* (2006.01)

(52) U.S. Cl.
CPC ...... *A61M 5/31513* (2013.01); *C10M 169/04* (2013.01); *A61M 5/31511* (2013.01);
(Continued)

(58) Field of Classification Search
None
See application file for complete search history.

(56) References Cited

U.S. PATENT DOCUMENTS 2,704,748 A * 3/1955 Pfeifer ............ C08K 5/14
524/588
2,980,475 A * 4/1961 Wolfe ............ C10M 7/00
384/278

(Continued)

FOREIGN PATENT DOCUMENTS

CN 101126417 A 2/2008
CN 101215398 7/2008
(Continued)

OTHER PUBLICATIONS

Multibase Silastic Q7-4735 Dow Corning, watweb.com, downloaded Sep. 5, 2015.*
(Continued)

*Primary Examiner* — Peter A Salamon
(74) *Attorney, Agent, or Firm* — Joseph Waters; McDonald Hopkins LLC

(57) ABSTRACT

In one aspect, a self-lubricating component is provided for a pharmaceutical packaging assembly. The self-lubricating component comprises a polymer composition and an effective amount of a lubricating additive such as, for example, boron nitride. In another aspect, a pharmaceutical packaging assembly may be provided having a surface thereof coated with a lubricating composition comprising boron nitride.
(Continued)

The pharmaceutical packaging composition may be, for example, a pre-filled syringe comprising a body (barrel) and a plunger assembly.

19 Claims, 3 Drawing Sheets

Related U.S. Application Data is a continuation-in-part of application No. 12/896,327, filed on Oct. 1, 2010, now Pat. No. 8,618,185.

(60) Provisional application No. 61/247,770, filed on Oct. 1, 2009.

(52) U.S. Cl.
CPC .............. *A61M 2005/3131* (2013.01); *C10M 2201/041* (2013.01); *C10M 2201/061* (2013.01); *C10M 2201/066* (2013.01); *C10M 2201/103* (2013.01); *C10M 2201/105* (2013.01); *C10M 2205/20* (2013.01); *C10M 2205/203* (2013.01); *C10M 2207/126* (2013.01); *C10M 2207/28* (2013.01); *C10M 2207/283* (2013.01); *C10M 2213/062* (2013.01); *C10M 2215/08* (2013.01); *C10M 2229/02* (2013.01); *C10M 2229/025* (2013.01); *C10M 2229/04* (2013.01); *C10M 2229/051* (2013.01); *C10N 2230/06* (2013.01); *C10N 2240/66* (2013.01)

(56) References Cited

U.S. PATENT DOCUMENTS

| | | | |
|---|---|---|---|
| 3,012,982 A * | 12/1961 | Toullec | C08G 12/00 524/765 |
| 3,261,800 A * | 7/1966 | Collins, III | C08K 3/38 250/518.1 |
| 4,087,343 A * | 5/1978 | Custer | C25B 9/142 204/219 |
| 4,760,116 A | 7/1988 | Roberts | |
| 5,153,039 A | 10/1992 | Porter et al. | |
| 5,248,333 A * | 9/1993 | Worschech | C08K 5/20 106/38.24 |
| 5,331,019 A * | 7/1994 | Payne, Jr. | A61L 2/08 522/157 |
| 5,356,948 A * | 10/1994 | Payne, Jr. | A61L 2/08 522/155 |
| 5,413,563 A | 5/1995 | Basile et al. | |
| 5,693,305 A * | 12/1997 | Revankar | C30B 29/403 423/412 |
| 5,782,815 A | 7/1998 | Yanai et al. | |
| 6,027,481 A | 2/2000 | Barrelle et al. | |
| 6,296,893 B2 | 10/2001 | Heinz et al. | |
| 6,660,241 B2 * | 12/2003 | Clere | B29C 47/0004 423/290 |
| 6,746,430 B2 * | 6/2004 | Lubrecht | A61L 31/10 427/487 |
| 6,939,576 B2 * | 9/2005 | Deshpande | B05D 1/08 427/223 |
| 6,951,583 B2 * | 10/2005 | Clere | B29C 47/0004 106/287.3 |
| 7,077,826 B1 * | 7/2006 | Gray | A61M 5/3135 604/171 |
| 7,648,487 B2 * | 1/2010 | Ito | A61M 5/3129 604/230 |
| 8,492,319 B2 | 7/2013 | Malshe et al. | |
| 8,530,536 B2 * | 9/2013 | Conzone | A61M 5/31513 522/75 |
| 8,618,185 B2 * | 12/2013 | Conzone | A61M 5/31513 522/75 |
| 2001/0004466 A1 * | 6/2001 | Heinz | A61L 29/085 427/2.1 |
| 2002/0051596 A1 | 5/2002 | Yamamoto et al. | |
| 2003/0148030 A1 * | 8/2003 | Vernon, Jr. | A61M 5/31513 427/255.28 |
| 2003/0180484 A1 * | 9/2003 | Imai | C10M 111/04 428/34.1 |
| 2005/0070848 A1 * | 3/2005 | Kim | A61M 5/2053 604/140 |
| 2006/0142525 A1 * | 6/2006 | Lai | A61L 27/165 351/159.33 |
| 2006/0200084 A1 * | 9/2006 | Ito | A61M 5/3129 604/230 |
| 2006/0264897 A1 * | 11/2006 | Lobl | A61M 39/0208 604/506 |
| 2007/0037898 A1 * | 2/2007 | Phelan | G02B 1/043 351/159.33 |
| 2007/0088291 A1 * | 4/2007 | Weilbacher | A61M 5/31513 604/218 |
| 2007/0148326 A1 * | 6/2007 | Hastings | A61M 5/31513 427/2.27 |
| 2007/0254000 A1 * | 11/2007 | Guo | A61L 29/049 424/422 |
| 2008/0167597 A1 * | 7/2008 | Dougherty | C08L 23/06 604/12 |
| 2008/0226930 A1 * | 9/2008 | Furuichi | B29C 66/73773 428/521 |
| 2008/0312111 A1 * | 12/2008 | Malshe | C10M 171/06 508/155 |
| 2009/0004231 A1 * | 1/2009 | Popp | A61K 9/1075 424/400 |
| 2009/0209922 A1 * | 8/2009 | Boisjoly | A61M 39/045 604/256 |
| 2012/0034428 A1 | 2/2012 | Clarke | |
| 2012/0065595 A1 * | 3/2012 | Conzone | A61M 5/31513 604/230 |
| 2013/0338606 A1 * | 12/2013 | Conzone | A61M 5/31513 604/230 |

FOREIGN PATENT DOCUMENTS

| | | |
|---|---|---|
| EP | 1028141 | 8/2000 |
| JP | 2006-182960 | 7/2006 |
| JP | 2009-523863 | 6/2009 |
| WO | 2007030630 | 3/2007 |
| WO | 2007082299 | 7/2007 |
| WO | WO2007030630 | 10/2008 |
| WO | WO2007082299 | 3/2009 |
| WO | 2012158408 | 11/2012 |
| WO | WO2012158408 | 11/2012 |

OTHER PUBLICATIONS

Silastic Q7-4735 TDS, Dow Corning, downloaded Sep. 5, 2015.*
Silastic Q7-4735 Saftey Data Sheet, Part A, Dow Corning, downloaded Sep. 5, 2015.*
Silastic Q7-4735 Saftey Data Sheet, Part B, Dow Corning, downloaded Sep. 5, 2015.*
Andersson, Marla M. et al., Stabilizing effect of chemical additives against oxidation of lactate dehydrogenase, Biotechnol. Appl. Biochem. (2000), vol. 32, pp. 145-153.
Ugurlu, Timucin et al., Hexagonal boron nitride as a tablet lubricant and a comparison with conventional lubricants, International Journal of Pharmaceutics 353 (2008) pp. 45-51.
International Search Report and the Written Opinion of the international Searching Authority, Momentive Performance Materials Inc., PCT/US2011/053845, Jan. 18, 2012.
European Extend Search Report, Momentive Performance Materials Inc., EP11829858.7, (PCT/US2011/053845), Feb. 7, 2014.
Chinese Office Action for Chinese Patent Application No. 201180047872.8 mailed Apr. 15, 2015.
Japanese Office Action for Japanese Patent Application No. 2013-531828, mailed Jul. 7, 2015.
European Office Action for European Patent Application No. 11 829 858.7-1662, dated Oct. 13, 2014.

(56) References Cited

OTHER PUBLICATIONS

Chinese Office Action for Chinese Patent Application No. 201180047872.8, dated Aug. 8, 2014.
International Search Report and Written Opinion for International Patent Application No. PCT/US2014/051210, mailed Dec. 4, 2014.
International Search Report and the Written Opinion of the International Searching Authority, Momentive Performance Materials Inc., PCT/US2014/051210, Dec. 4, 2014.
Office Action from State Intellectual Property Office of People's Republic of China, 201180047872.8, Aug. 8, 2014.
Communication from European Patent Office pursuant to Article 94(3) EPC, Oct. 13, 2014.

* cited by examiner

SELF-LUBRICATING PHARMACEUTICAL SYRINGE STOPPERS

CROSS REFERENCE TO RELATED APPLICATIONS

The present application claims priority as a continuation-in-part application to U.S. application Ser. No. 13/227,625, filed on Sep. 8, 2011, which is a continuation-in-part to U.S. application Ser. No. 12/896,327, filed on Oct. 1, 2010, which claims priority to U.S. Provisional Patent Application No. 61/247,770, filed on Oct. 1, 2009, each of which is incorporated by reference herein in its entirety.

FIELD OF INVENTION

The present invention relates to components for a pharmaceutical packaging assembly and a pharmaceutical packaging assembly comprising such components. In particular, aspects of the present invention relate to self-lubricating components adapted for sliding engagement with an interior surface of a pharmaceutical packaging assembly, or a packaging assembly coated with a lubricious coating layer.

BACKGROUND

There has been a recent trend in the pharmaceutical market toward the use of pre-filled injectable syringes. These syringes provide benefits of requiring less overfill than traditional syringes, reduced needle-stick injuries, and less risk of cross-infection. Because of these benefits, many of the expensive biological (protein-based) drugs are delivered via pre-filled injectables. However, syringes, unlike ampoules and vials, require a layer of lubricant inside the syringe barrel to facilitate the easy movement of the plunger. As shown in FIG. 1, extractables from the lubricant as well as the packaging containers can cause poisoning and reduced efficacy of these drugs (see, e.g., U.S. Pat. Nos. 5,782,815 and 6,027,481).

FIG. 1 is a schematic illustration of a syringe and the presence of extractables from a lubricant coating from the syringe barrel in injectables of the syringe. FIG. 1 illustrates a syringe containing a drug/biotherapeutic 2 and having a lubricating silicone oil layer 4. The silicone oil droplet 6 leaches into the dispersion, and precipitates as a drug precipitate 8-oligomers on silicone oil droplets.

The lubricants are required to ensure smooth and steady injection of the drug, and to minimize the push force required to administer the drug, once the needle is embedded into the patient's skin. Lack of lubrication can result in non-steady, or excessive force to extract the drug from the container resulting in sudden movement of the needle embedded in the patient's skin leading to pain or injury.

In addition, oxygen and moisture permeation through rubber stoppers can cause denaturing of the drug. That is, protein denaturation due to oxidation is well established in the literature (Anderson et al, Biotech. App. Biochem, v32, pp 145 (2000)). Ceramic fillers and other additives can be compounded with the polymer stoppers to reduce the oxygen and moisture permeation rates, thus minimizing denaturing due to exposure of the drug to these contaminants over time (see, e.g., U.S. Pat. No. 5,153,039).

The most widely used conventional lubricant for syringe stoppers is silicone oil. Challenges with silicone oil include (1) a high break-force due to migration of silicone oil from between the plunger and the tube during storage, and (2) interaction of the silicone oil with the biological drugs that results in agglomeration and denaturing, thus reducing drug efficacy. Some have addressed these issues by replacing the silicone oil with hard-baked silicone coatings, fluorocarbon films, and non-silicone coatings (e.g. TriboGlide™, which is based on perfluoropolyether chemistries). Although these coatings claim to address the break-force and denaturing issues, the addition of coatings into a manufacturing process adds cost and complexity.

Thus, a need exists for an effective lubrication alternative for stoppers in pharmaceutical applications.

SUMMARY

The present invention provides a pharmaceutical packaging assembly having one or more components moveable within a body of the assembly, wherein the one or more components exhibit excellent lubricity and stability without the side affects experienced with prior lubricated systems such as contamination of the packaging assembly's contents or "unwetting" of the packaging assembly body.

In one aspect, the present invention provides a self-lubricating component for use in pharmaceutical packaging assembly. The self lubricating component comprises a material comprising an effective amount of lubricating additive. Exemplary lubricating additives include boron nitride (BN) and polytetrafluoroethylene (PTFE).

In another aspect, the present invention provides a pharmaceutical packaging assembly comprising a barrel having an interior surface coated with a composition comprising a lubricating additive. The lubricating additive may include boron nitride. The pharmaceutical packaging assembly may further include a plunger, and the plunger may optionally be coated with a lubricating composition or may be formed from a self-lubricating material comprising a lubricating additive.

Aspects of the present invention may be further understood with reference to the following detailed description.

DETAILED DESCRIPTION

The present technology relates to a pharmaceutical packaging assembly having one or more components moveable within the assembly. In one embodiment, the pharmaceutical packaging assembly may be adapted for dispensing a liquid such as medicaments, pharmaceuticals, and the like. In one embodiment, the assembly is designed for the liquid or dry (lyophilized) storage of drugs. For example, the pharmaceutical packaging assembly may comprise a syringe, and, in embodiments, the syringe may be a pre-filled syringe.

Figure 1:
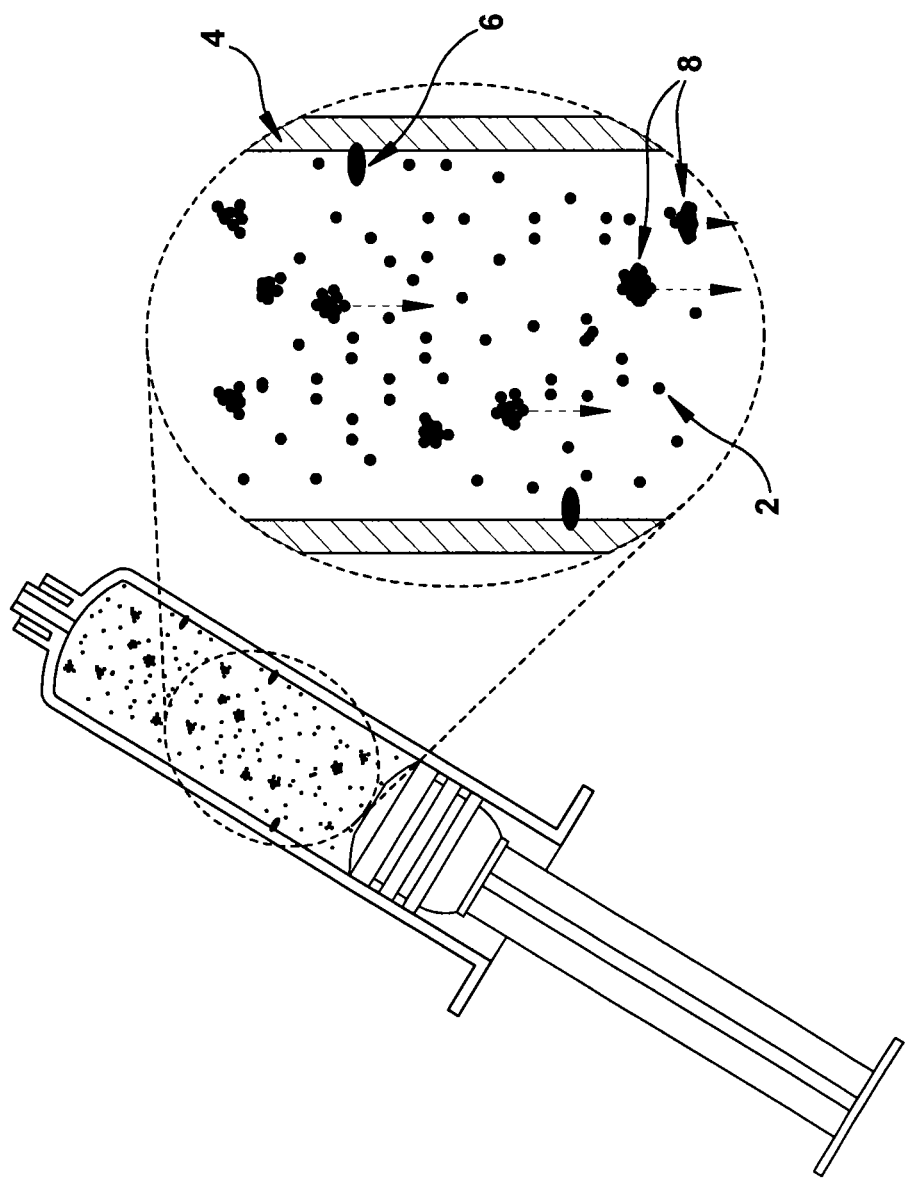
FIG. 1 is a schematic illustration of a syringe and the presence of extractables from a lubricant coating from the syringe barrel in injectables of the syringe.
Figure 2:
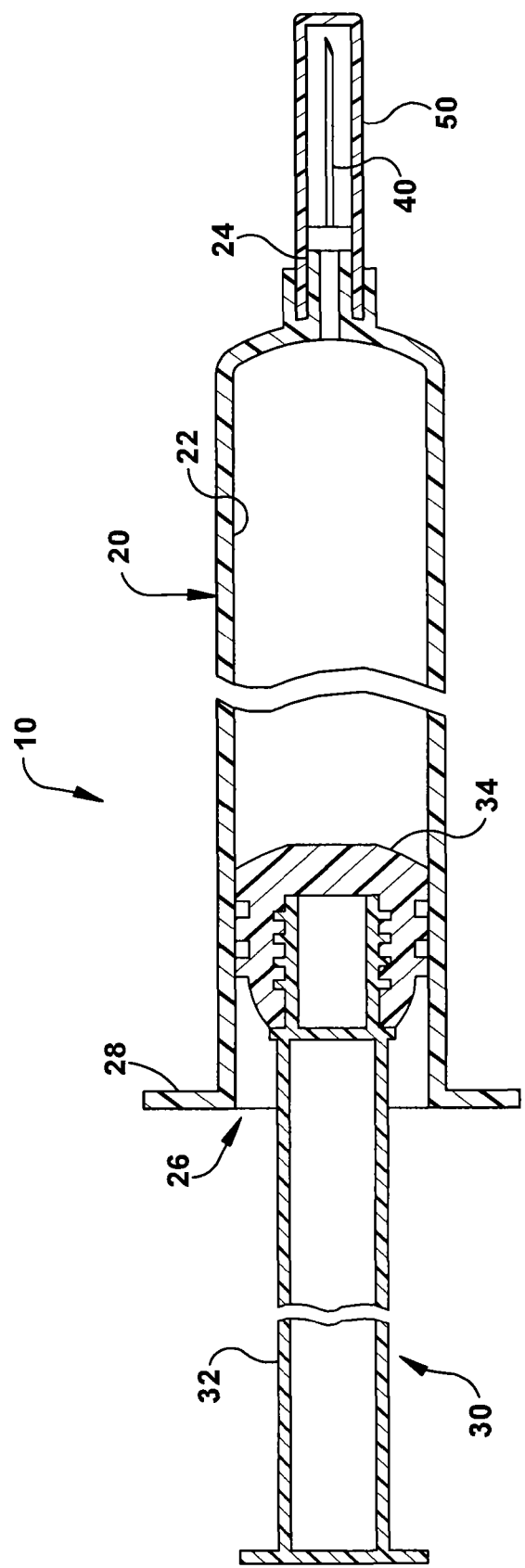
FIG. 2 is a cross section of a pre-filled syringe in accordance with aspects of the present invention.

Referring to FIG. 2, a non-limiting embodiment of a pharmaceutical packaging assembly 10 is shown in the form of a syringe (also referred to by numeral 10). The syringe 10 includes a body 20 for housing a fluid and a plunger assembly 30. The body 20 includes an inner wall or surface 22, a distal end terminating in a tapered tip 24, and a proximal end 26 for receiving the plunger assembly 30. Disposed about the periphery of the distal end 26 is flanged portion 28, which may also be referred to as a finger hub, to facilitate holding the body 20 during operation of the plunger. A needle assembly 40 is connected to the tip 24. The packaging assembly may further comprise a removable cover 50 disposed about the needle 40 and the tip 24 to protect the contents of the syringe prior to use, especially when provided as a pre-filled syringe.

The plunger assembly 30 includes a plunger rod 32 and a plunger 34. The plunger assembly is generally adapted to be slideably positioned in the body 20. The plunger assembly is typically sized to closely fit within the body 20 to reduce or eliminate leakage of a fluid housed in the body 20. The syringe may be operated by exerting a force on the plunger rod 32, which drives the plunger and forces the fluid housed in the body to be dispensed through the tip 24 and out the needle 40. The plunger 34, which may also be referred to herein as a stopper, may be formed from a material chosen from, for example, a rubber, a plastic, or a silicone material. The plunger rod 32 may be formed of any suitable material including a rubber, a plastic, a glass, or the like.

In accordance with aspects of the present invention, one or more of a portion of the body of the pharmaceutical package and a moveable component (such as the plunger/plunger assembly) of the packaging assembly is provided to exhibit sufficient lubricity for the moveable component to be suitably moveable within the packaging assembly body to perform its desired function (e.g., the sliding engagement of the plunger on the inner surface of the syringe body to force liquids out of the syringe). In one embodiment, a moveable component may be formed from a self-lubricating material to provide a self-lubricating component. Referring to FIG. 2, for example, an embodiment of the packaging assembly 10 may include a plunger 34 formed from a self-lubricating material. The self-lubricating material may comprise, for example, a self-lubricating rubber, plastic, or silicone comprising a lubricious additive or filler. Suitable lubricating additives or fillers include those from the following: boron nitride, graphite, molybdenum disulfide, talc, mica, colloidal silica, fumed silica, high molecular weight silicone gum, Reimer's salt, siloxane particles (including, for example, methylsilsesquioxane micro-fine resin particles such as those sold under the tradename Tospearl™), any salt, ester, or amide of a fatty acid, vinylfluoro silicones, D4, or combinations of two or more thereof. Boron nitride is an exemplary lubricating additive and provides excellent results. Examples of suitable salts, esters, or amides of fatty acids include, but are not limited to, zinc stearate, oleamide, erucamide, pentaerythritol stearate, and the like. A particularly suitable lubricating additive is hexagonal boron nitride (hBN). The lubricating filler provides self-lubricating properties to the plunger, thus eliminating the need to add lubricating coatings, such as silicone oil, baked silicone, or fluorocarbon coatings.

The amount of filler loading in the self-lubricating material may range from about 0.1 to 50% by weight. In one embodiment the filler loading is from about 3 to about 20% by weight. In another embodiment, the filler loading is from about 5 to about 10% by weight.

The base material for forming the self-lubricating material may be selected as desired. In the case of a polymer material, the polymer may be any conventional material suitable for use as a syringe plunger. Non-limiting, exemplary materials include natural rubber, silicone elastomers, thermoplastic elastomers, isobutylene or polybutadiene rubber, polytetrafluoroethylene, fluorosilicone rubbers, chlorinated polyethylene elastomers, ethylene vinyl acetate, hexafluoropropylene-vinylidene fluoride-tetrafluoroethylene terpolymers (e.g., materials sold under the tradename Fluorel™ and Viton™), butyl rubbers, synthetic polyisoprene rubber, styrene-butadiene rubbers, tetrafluoroethylene propylene copolymers, thermoplastic-copolyesters, and the like. Methods for compounding the filler in the base material (e.g., a polymer material) may be any known in the art.

In another aspect, at least a portion of a surface of the pharmaceutical packaging assembly is coated with a filled polymeric coating composition comprising a lubricating additive. The lubricating additive may be chosen from materials including the following: Boron nitride, graphite, molybdenum disulfide, talc, mica, colloidal silica, fumed silica, high molecular weight silicone gum, Reimer's salt, siloxane particles (e.g., Tospearl™), vinylfluoro silicones, D4, or combinations of two or more thereof. A particularly suitable filler is hBN.

Referring again to FIG. 2 for example, in one embodiment the inner surface 22 of the body 20 may be coated with the filled coating. In another embodiment, at least a portion of plunger assembly including the surface of the plunger rod 32 or the plunger 34 may be coated with the filled coating. It will also be appreciated that a packaging assembly could be provided comprising a body with an inner surface thereof coated with an filled coating, and a plunger formed from a self-lubricating material.

As previously described with respect to the self-lubricating material (as may be used with, for example, the plunger), the amount of lubricating additive (e.g., BN or others) in the coating may range from about 0.1 to about 50% by weight, from about 3 to about 20% by weight, and even from about 5 to about 10% by weight. The polymer may be any conventional material suitable for use as a syringe plunger. Non-limiting exemplary materials include silicone elastomers, thermoplastic elastomers, isobutylene or polybutadiene rubber, or polytetrafluoroethylene.

The body of the pharmaceutical package may be formed from any suitable material. Non-limiting examples of suitable materials include glass, cyclic olefin copolymers, polymethylpentene, polyethylene, polypropylene, polystyrene, acrylic and mehtacrylic polymers, and the like. The degree of transparency or opacity of the body may also be selected as desired.

Due to its hexagonal structure, hBN is extremely lubricious, with a coefficient of friction of 0.2. BN is an inert, non-toxic material, and is expected to have minimal or no adverse interactions with the biological drugs, making it an excellent choice for the present embodiments.

Because the self-lubricating plunger is inherently lubricating, it is expected to have a minimal break-force, and will ensure a smooth and consistent actuation during drug delivery. Additionally, because of the excellent lubricating properties of boron nitride, the overall force required to depress the plunger and inject the drug will be reduced, thus minimizing the probability of injury and pain to the patient due to quick movements of the needle embedded into the patient's skin.

Further, adding BN powders to the polymeric resins should also reduce oxygen and moisture permeation rate. Similarly adding BN platelets to resins should have an added benefit of reducing the resin permeability. That is, it is known that adding platy/flaky talc powders to various resins (rubbers/elastomers and thermoplastics) will reduce permeability of oxygen through the resin.

In another aspect, BN polymeric coatings and composite coatings comprising boron nitride may be applied to a conventional syringe plunger and/or the syringe barrel wall in place of the traditional silicone oil coating for lubrication.

Boron nitride coatings can be applied to either the tube or the plunger/stopper or both. Boron nitride coatings can be applied as a paint, or through various deposition processes such as chemical vapor deposition, plasma-enhanced chemical vapor deposition, chemical liquid deposition, ion-plasma deposition, physical vapor deposition, electron beam deposition, electroplating, etc.

Results

Figure 3:
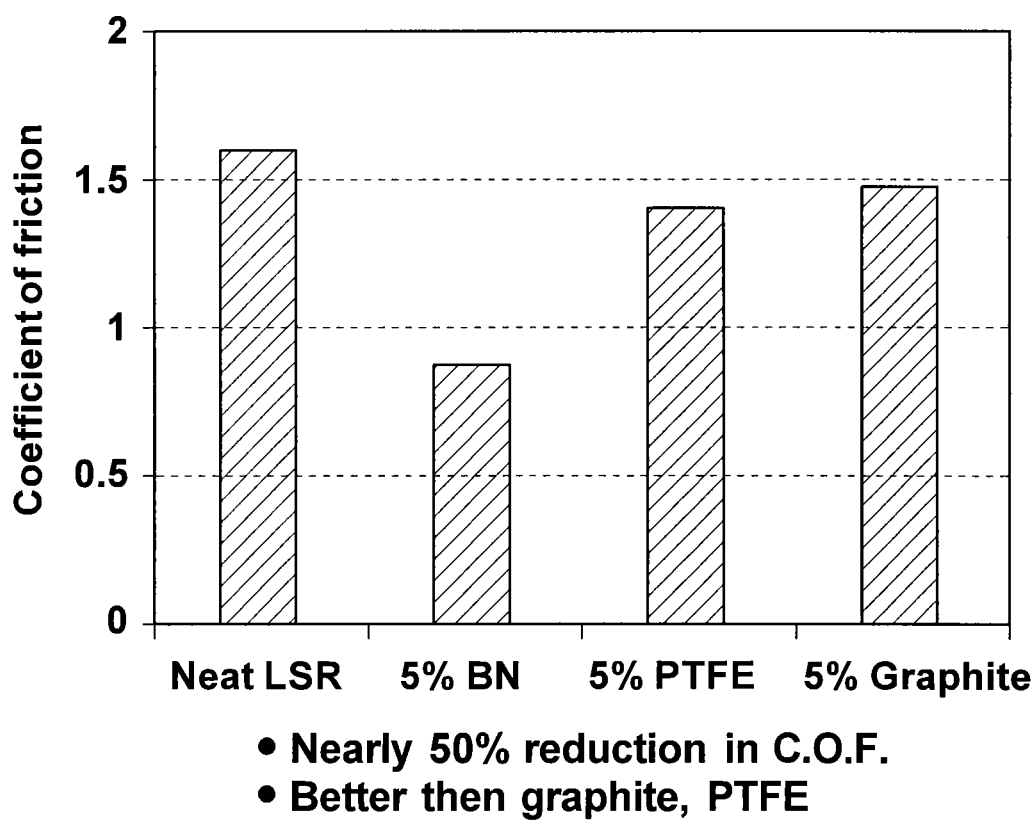
FIG. 3 is bar graph comparing the coefficient of friction of a silicone coating composition comprising different fillers.

Boron nitride, graphite, and PTFE fillers were compounded at 5 wt. % into neat liquid silicone rubber "Neat LSR" silicone, and the coefficient of friction was measured on the resulting composites. As seen in FIG. 3, while all fillers showed some lubricating improvement over non-filled silicone, results showed that addition of hBN to the LSR reduced the coefficient of friction by approximately 50%, significantly better than that of the graphite and PTFE fillers.

While aspects of the invention have been described with respect to a syringe, it will be appreciated that the pharmaceutical package and the moveable component(s) are not limited to a syringe and a plunger, respectively. In addition to its use as a plunger in syringes, self-lubricating materials such as, for example, BN filled polymers, may find application where low friction forces are desired, and the use of an inert, immobile lubricant system is appropriate. The following is a partial list:

Barrel Syringe Manufacturing
Glass Syringe Lines for Prefilled Insulin
Glass Bottles & Specialty Chemistry Containers of High Value and/or Controlled Dose Fluid can benefit from this technology.
Films that prevent wetting of the glass surface will reduce residual fluid in container.
Infusion Therapy
Contrast Media Market
Radioactive and Specialty Chemistries
Syringe Pump Components
Stoppers
Vial Coating
Electronic Leads & Contacts
Mechanical Valves, Ceramic Valves, Medical Valves
Mold Release Applications
Needle Lubrication
Catheter Lubrication
Plastic Threaded Components & Caps
Surgical Shields
Surgical Probes
Endoscope Lubrication
Elastomer Seals and/or Gaskets for Medical Devices
Surgical Cameras
Needle-free Access Valves In addition to improved lubrication behavior, formulations may be modified to include additional functionality to the resin composition. For example, in addition to the low coefficient of friction, it may be desirable for the resin to have low wear/high resistance to abrasion, low permeability to moisture, oxygen and other gases, high thermal conductivity, low compression set, controlled haptic sensation, etc. Various embodiments to achieve such formulations are discussed here below.

Low Wear/High Abrasion Resistance:

The wear characteristic of a material is a measure of how much mass or volume is worn off when in sliding contact with a mating surface. Excessive wear is usually undesirable because it may lower the lifetime of the component and may also introduce undesirable particulate debris if in contact with any fluids. While lowering the coefficient of friction may itself help improve or reduce the wear of a material, it may be beneficial to include other hard fillers to minimize the amount of material is abraded. Non-limiting examples of suitable hard fillers include alumina, silica, titania, magnesia, zinc oxide, silicon carbide, silicon nitride, tungsten carbide, cubic boron nitride, aluminum nitride, etc., or a combination of two or more thereof. In one embodiment, it may be sufficient if the hardness (as measured on any relevant scale such as Mohs hardness or Vicker's hardness) of the "hard" fillers is greater than the hardness of the mating surface (e.g., the interior surface of a pharmaceutical package such as a barrel). Additionally, the particle size of these hard particle fillers may be of the order of microns, sub-micron or even in the nano-scale.

In one embodiment, the resin composition comprises up to 20 vol % of a lubricating additive and up to 10 vol % of a hard filler. Examples of the lubricating additives may be those mentioned previously such as boron nitride, graphite, telfon/PTFE powders, Reimer's salt, high molecular weight silicone gums, D4, fatty acid derivatives etc. In another embodiment, the composition comprises up to 15 vol % of a lubricating additive, and up to 5 vol % of an additional hard filler. In another embodiment, the composition comprises up to 10 vol % of the lubricating additive, and up to 3 vol % of the hard filler. In yet another embodiment, the composition contains up to 5 vol % of the lubricating filler and up to 2 vol % of the hard filler. In one embodiment, the resin composition comprises from about 0.01 vol % to about 20% vol of a lubricating additive and from about 0.01 vol % to about 15 vol % of a hard filler. In another embodiment, the resin composition comprises from about 0.1 vol % to about 10% vol of a lubricating additive and from about 0.1 vol % to about 7 vol % of a hard filler. In still another embodiment, the resin composition comprises from about 0.5 vol % to about 5% vol of a lubricating additive and from about 0.5 vol % to about 5 vol % of a hard filler. Here as elsewhere in the specification and claims, numerical values can be combined to form new and non-disclosed ranges.

To any of the above-mentioned embodiments, a third optional reinforcing additive may be included in the composition such as, but not limited to, carbon fiber, glass fiber, aramid fiber, fibrous minerals such that combine silicates of calcium, magnesium, aluminum, iron etc., or other natural or synthetic vitreous fibers, or a fumed metal oxide such as fumed silica, fumed titania, fumed alumina, etc., or a combination of two or more reinforcing additives. In one embodiment, the composition may contain up to 20 vol % of an additional reinforcing additive. In one embodiment, the composition comprises from about 0.5 vol % volume to about 40 vol % volume of a reinforcing additive; from about 3 vol % to about 30 vol % volume of a reinforcing additive; even from about 5 vol % to about 20 vol % of a reinforcing additive. Here as elsewhere in the specification and claims, numerical values can be combined to form new and non-disclosed ranges.

In any of the above compositions, the particle size of one or more of the additives may be in the micron-, sub-micron- or nano-scale. Some of the fillers, especially the reinforcing fillers, may optionally have a high aspect ratio, say up to 10, up to 50, up to 100, up to 300, or even up to 1000. It may be possible to combine some of the above functionalities by utilizing unique fillers such fibers of alumina, silicon carbide, silicon nitride, glass/silica to combine the reinforcing and hard filler functions into a single material. It will be appreciated that, the composition may contain a combination of two or more of the hard fillers or reinforcing fillers.

In addition to the composition of the resin, the surface finish of the final component can be examined or controlled as this too may influence wear behavior of the part or component. In one embodiment, the wear of the resin composition may be less than $50 \times 10^{-6}$ mm$^3$/Nm, or less than $30 \times 10^{-6}$ mm$^3$/Nm, or less than $10 \times 10^{-6}$ mm$^3$/Nm, or less than $5 \times 10^{-6}$ mm$^3$/Nm, or less than $2 \times 10^{-6}$ mm$^3$/Nm or even less than $1 \times 10^{-6}$ mm$^3$/Nm. In one embodiment, the wear of the resin is from about $0.1 \times 10^{-6}$ mm$^3$/Nm to about $50 \times 10^{-6}$ mm$^3$/Nm, even from about $0.5 \times 10^{-6}$ mm$^3$/Nm to about $30 \times 10^{-6}$ mm$^3$/Nm Low Permeability:

In addition to low coefficient of friction, it may be beneficial in some applications to have a composition with low permeability. The permeability of resins may be reduced with the use of high-aspect fillers. High-aspect ratio platelets may be especially useful for this purpose. Such fillers, if well distributed in the matrix, make the diffusion path for gases or water vapor highly tortuous and minimize the rate of diffusion through the material. Non-limiting examples of such materials are clays, exfoliated clays, graphite, exfoliated graphite, graphene, hBN, exfoliated hBN, boron nitride nanosheets, layered silicates such as kaolinites, montmorillonites, smectites, vermicullites, mica, hydrous mica, etc., or aluminates such as sodium aluminate, beta-alumina, calcium aluminates. In one embodiment, the high aspect ratio filler has an aspect ratio of from about 3 to about 1000; from about 10 to about 300; even from about 20 to about 100.

In one embodiment, in addition to a lubricating additive, the composition contains up to 10 vol % of a high aspect ratio platelet (HARP) filler, up to 30 vol %, or up to 50 vol % or even up to 70 vol % of a HARP filler. In one embodiment, the composition comprises from about 0.5 vol % to about 40 vol % of a HARP filler; from about 1 vol % to about 30 vol % of a HARP filler, even from about 5 vol % to about 10 vol %. The above compositions may employ a combination of two or more of the HARP fillers.

In one embodiment, the permeability of the composition may be less than 1000 barrers, less than 500 barrers, less than 200 barrers, less than 100 barrers, even less than 50 barrers. In one embodiment, the composition has a permeability of from about 20 barrers to about 1000 barrers; from about 50 barrers to about 800 barrers; from about 100 barrers to about 500 barrers; even from about 200 barrers to about 300 barrers. The challenge with the formulations is to retain sufficient characteristics of the original resin that still enable use in the application. High loadings of such HARP fillers may lead to decreased elasticity (defined by strain at break), increased flexural and tensile moduli, increased hardness (Shore 00, Shore A or Shore D or equivalent). In one embodiment, the material has a Shore A hardness less than 80, less than 40, or even less than 20. In one embodiment, the material has a Shore 00 hardness less than 70, less than 50 or even less than 30.

The following examples in Table 1 demonstrate non-limiting embodiments of compositions to achieve low permeability. In the embodiments, an exfoliated clay is added to a silicone elastomer composition. The clay used in these formulations is Cloisite™ 30B, available from Southern Clay Products/Rockwood additives, which is suitably exfoliated while compounding into the silicone resin.

TABLE 1

| Formulation | Oxygen Permeability (barrers) |
| --- | --- |
| LSR2050 (silicone elastomer) | 1000 |
| LSR2050 + 2 wt. % exfoliated clay | 379 |
| LSR2050 + 4 wt. % exfoliated clay | 424 |

High Thermal Conductivity:

Self-lubricating compositions may also benefit from high thermal conductivity in some applications. Higher thermal conductivity may, for example, help dissipate hot spots generated by friction and can help increase the life time of the component. It will be appreciated that the compositions can comprise a plurality of thermally conductive fillers. In one embodiment, the thermally conductive filler is chosen from boron nitride (hexagonal or cubic), silica, glass fibers, a metal oxide such as, zinc oxide, magnesium oxide, beryllium oxide, titanium oxide, zirconium oxide, etc., calcium carbonate, talc, mica, wollastonite, clays, exfoliated clays, alumina, aluminum nitride, graphite, metallic powders, e.g., aluminum, copper, bronze, brass, etc., glass flake, or other high aspect ratio fibers, rods, or flakes, magnesia, titania, fibers or whiskers of carbon, silicon carbide, silicon nitride, nano-scale fibers such as carbon nanotubes, graphene, boron nitride nanotubes, boron nitride nanosheets, zinc oxide nanotubes, etc., or a combination of two or more thereof. In one embodiment, the thermally conductive filler has a low electrical conductivity or is electrically insulating.

In one embodiment, the composition has an in-plane thermal conductivity of at least 0.3 W/mK, at least 0.6 W/mK, at least 1 W/mK, at least 3.5 W/mK, at least 5 W/mK, at least 10 W/mK, even at least 30 W/mK. In one embodiment, the through-plane thermal conductivity may be at least 0.3 W/mK, or at least 0.6 W/mK, or at least 1 W/mK, or at least 2 W/mK, or at least 3.5 W/mK, or at least 5 W/mK, or at least 10 W/mK. The composition may be tuned to achieve the right combination of in-plane and through-plane thermal conductivity that may be best for the application.

Low Compression Set:

Good compression set can be a useful material property for some applications, especially where the component may experience repeated compression cycles. A low compression set is usually desirable and may help extend the life time of the component. The self-lubricating compositions discussed above may include other additives that would lower the compression set. Non-limiting examples of material suitable for lowering compression set include a clay or other mineral fillers, boron nitride or other ceramic fillers, or a combination of two or more thereof. In one embodiment, the composition may contain up to 0.05 wt. % of a clay, up to 1 wt. %, up to 2 wt. %, up to 5 wt. %, up to 10 wt. %. In one embodiment, the composition comprises from about 0.05 wt. % to about 10 wt. % of a clay, even from about 1 wt. % to about 5 wt. %. However, it may be possible to achieve a low compression set with the use of some lubricating additives such as hexagonal boron nitride, graphite, MoS$_2$, wurtzitic-ZnS, tin sulfide etc.

In one embodiment, the composition has a compression set less than 50%, less than 30%, even less than 20%. In one embodiment, the composition has a compression set of from about 3% to about 50%; from about 5% to about 30%; even from about 10% to about 20%.

Non-limiting embodiments of compositions with a low compression set are illustrated in Table 2. As shown in Table 2, adding a claim such as an exfoliated clay can reduce the compression set of the composition. The clay used in these formulation is Cloisite™ 30B, available from Southern Clay Products/Rockwood additives, which is suitably exfoliated while compounding into the silicone resin.

TABLE 2

| Formulation | Compression set |
| --- | --- |
| LSR2050 (silicone elastomer) | 66 |
| LSR2050 + 1 wt. % exfoliated clay | 23 |
| LSR2050 + 2 wt. % exfoliated clay | 22 |

Controlled Haptic Sensation: In addition to low coefficient of friction, it may also be beneficial to improve the haptic sensation or sensory feel of the surface of the material/part. The haptic feel can be adjusted with the use of fillers & additives or controlling the surface finish during the molding step. The self-lubricating compositions discussed above may contain optional additives and/or fillers such as boron nitride, allantoin, arrowroot powder, various types of clays such as bentonite, kaolin, French green clay, red clay etc., cyclomethicone, dimethicone, various types of starch powders or flour such as tapioca starch powder or corn flour, fatty acids or fatty acid derivatives such as stearic acid, magnesium stearate, zinc stearate, oleamide, erucamide etc., silicone resins, gums or particles, other additives such as Tospearl™, Velvesil™, Velvesil FX™ (available from Momentive™) etc. In one embodiment, the composition contains an additional 0.5 wt. % to 50 wt. %, or 1 to 30 wt. % or 3 to 20 wt. % or 5 to 15 wt. % of such an additive.

The roughness of the part can be tuned by imparting a controlled surface roughness in the molding step. The mold may be suitably prepared to deliver a desired surface roughness. In one embodiment, the part has an average surface roughness ($R_a$) of 500 microns or less, or 300 microns or less, or 100 microns or less, or even 50 microns or less. It would be obvious to one skilled in the art that the surface roughness may be characterized by other suitable measures such as $R_{RMS}$, $R_v$, $R_p$, $R_t$, $R_{sk}$, $R_{ku}$ etc. of the surface.

Embodiments of the invention have been described above and modifications and alterations may occur to others upon the reading and understanding of this specification. The claims as follows are intended to include all modifications and alterations insofar as they come within the scope of the claims or the equivalent thereof.

What is claimed is:

1. A self-lubricating component for a pharmaceutical packaging assembly comprising a polymer composition comprising:
    a lubricating additive, wherein the lubricating additive comprises one or more of: boron nitride, graphite, molybdenum disulfide, talc, mica, colloidal silica, fumed silica, high molecular weight silicone gum, Reimer's salt, siloxane particles, vinylfluoro silicones, a salt, ester, or amide of a fatty acid, or any combination of two or more thereof;
    wherein the polymer composition has a compression set of less than 20%.

2. The component of claim 1 in the form of a plunger, piston, diaphragm, or valve disc for medical equipment.

3. The component of claim 1, wherein the lubricating additive is present in an amount of from about 0.1 to about 50% by weight of the polymer composition.

4. The component of claim 1, wherein the lubricating additive is present in an amount of from about 5 to about 20% by weight of the polymer composition.

5. The component of claim 1, wherein the lubricating additive is present in an amount of from about 10 to about 15% by weight of the polymer composition.

6. The component of claim 1 further comprising a reinforcing additive.

7. The component of claim 6, wherein the reinforcing additive is chosen from carbon fiber, glass fiber, aramid fiber, a fibrous minerals, a vitreous fiber, a fumed metal oxide, or a combination of two or more thereof.

8. The component of claim 6, comprising the reinforcing additive in an amount of from about 0.1 to about 20% by weight of the polymer composition.

9. The component of claim 1, wherein the lubricating additive comprises hexagonal boron nitride.

10. The component of claim 6, wherein the reinforcing additive is a high aspect filler having an aspect ratio of from about 10 to about 300.

11. The component of claim 10, wherein the high aspect filler is chosen from a clay, an exfoliated clay, a graphite, an exfoliated graphite, graphene, exfoliated boron nitride, boron nitride nanosheets, a layered silicate, an aluminate, or a combination of two or more thereof.

12. The component of claim 10, wherein the polymer composition comprises the high aspect filler in an amount of from about 1 vol % to about 70 vol %.

13. The component of claim 1 comprising a clay.

14. The component of claim 1 comprising a clay in an amount of from about .05 wt. % to about 10 wt. %.

15. The component of claim 1 wherein the polymer composition further comprises a hard filler.

16. The component of claim 15 wherein the hard filler is chosen from alumina, silica, titania, magnesia, zinc oxide, silicon carbide, silicon nitride, tungsten carbide, cubic boron nitride, aluminum nitride, or a combination of two or more thereof.

17. A self-lubricating component for a pharmaceutical packaging assembly wherein the self-lubricating component is formed by a polymer composition comprising:
    a lubricating additive, wherein the lubricating additive comprises one or more of: boron nitride, graphite, molybdenum disulfide, talc, mica, colloidal silica, fumed silica, high molecular weight silicone gum, Reimer's salt, siloxane particles, vinylfluoro silicones, a salt, ester, or amide of a fatty acid, or any combination of two or more thereof;
    wherein the polymer composition has a permeability of less than 500 barrers.

18. The component of claim 17 wherein the polymer composition further comprises a hard filler.

19. The component of claim 18 wherein the hard filler is chosen from alumina, silica, titania, magnesia, zinc oxide, silicon carbide, silicon nitride, tungsten carbide, cubic boron nitride, aluminum nitride, or a combination of two or more thereof.

* * * * *